(12) United States Patent
Tucek

(10) Patent No.: US 7,883,533 B2
(45) Date of Patent: Feb. 8, 2011

(54) METHOD AND APPARATUS FOR ELECTROLYTIC HYDROTHERAPY

(75) Inventor: Kevin B Tucek, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 513 days.

(21) Appl. No.: 12/075,383

(22) Filed: Mar. 10, 2008

(65) Prior Publication Data

US 2008/0161869 A1 Jul. 3, 2008

Related U.S. Application Data

(63) Continuation-in-part of application No. 10/346,149, filed on Jan. 15, 2003, now Pat. No. 7,341,597.

(51) Int. Cl.
*A61H 21/00* (2006.01)

(52) U.S. Cl. ...................................... 607/86

(58) Field of Classification Search .................. 604/20; 607/2–3, 85–86; 205/742–761, 701; 210/748.01, 210/748.16–748.18, 749, 764
See application file for complete search history.

(56) References Cited

U.S. PATENT DOCUMENTS

| | | | | |
|---|---|---|---|---|
| 2,263,205 A | | 11/1941 | Conrad | |
| 3,616,355 A | * | 10/1971 | Themy et al. | 205/701 |
| 3,752,747 A | * | 8/1973 | Treharne et al. | 205/744 |
| 4,291,125 A | * | 9/1981 | Greatbatch | 424/618 |
| 4,337,136 A | * | 6/1982 | Dahlgren | 204/242 |
| 4,492,618 A | * | 1/1985 | Eder | 205/701 |
| 4,654,071 A | * | 3/1987 | Muller | 205/688 |
| 4,850,956 A | * | 7/1989 | Bontemps | 604/20 |
| 5,282,940 A | * | 2/1994 | Griffis et al. | 426/237 |
| 5,603,843 A | * | 2/1997 | Snee | 210/748.18 |
| 5,741,317 A | * | 4/1998 | Ostrow | 607/85 |
| 6,555,071 B2 | * | 4/2003 | Skrinjar | 422/186 |
| 7,341,597 B2 | * | 3/2008 | Tucek | 607/86 |

\* cited by examiner

*Primary Examiner*—Mark W Bockelman
(74) *Attorney, Agent, or Firm*—Etherton Law Group, LLC; Benjamin D. Tietgen; Sandra L. Etherton

(57) ABSTRACT

A device and method for increasing the number and type of ions in a hydrotherapy treatment to assist in removing unwanted chemicals from the body. A battery-powered array is submerged into a liquid foot bath to generate ions through electrolysis. The array has at least two electrodes, one containing copper and/or zinc, the other steel. The device can be run in two modes, thereby creating different types of ions and enabling the removal of different types of chemicals. The device uses a current and voltage regulator to deliver a regulated amount of current into the array regardless of the conductivity of the liquid, and electrical circuitry is used to control the duration and mode of the treatment. Excessive heat is dissipated with a heat sink.

9 Claims, 5 Drawing Sheets

METHOD AND APPARATUS FOR ELECTROLYTIC HYDROTHERAPY

CROSS-REFERENCE TO RELATED APPLICATIONS

This application claims the benefit of and is a continuation-in-part of application Ser. No. 10/346,149 filed Jan. 15, 2003, now U.S. Pat. No. 7,341,597.

FIELD OF INVENTION

This invention relates generally to hydrotherapy and particularly for the use of electrolysis of water to increase the number and types of ions available to assist in removing unwanted chemicals from the body.

BACKGROUND

Warm baths, mineral hot springs, and other forms of hydrotherapy have been known throughout the ages to aid in healing. The warm water relaxes muscles and opens the pores of the skin to enable unwanted chemicals to be released from the body and desired chemicals to be absorbed through the skin. The chemicals may be any atom, ion, or molecule, including complex chemical compounds found in the body, such as pathogens, antibodies, toxins, and pollutants. Herbs, other botanicals, and salts are commonly added to the water to create ions that help draw the unwanted chemicals from the body and then bond with the undesirable chemicals to prevent reabsorption into the body.

For example, metals may exert toxicity on cells by interfering with cell metabolism. Some metals form a complex with enzymes, and the resulting metal-enzyme complex may change the catalytic functional characteristics of the enzyme and thereby block the metabolic process within the cell. The stronger electronegative metals (such as copper, mercury and silver) bind with various groups of enzymes, thus blocking enzyme activity. Another mechanism of action of some heavy metals (gold, cadmium, copper, mercury, lead) is to combine with the cell membranes, altering membrane permeability. Other undesirable chemicals displace elements that are important structurally or electrochemically to cells, which then can no longer perform their biologic functions. Drawing the undesirable metals from the body and preventing them from being reabsorbed through ionic, covalent, chelating, metal-complexing and other chemical reactions with other chemicals may improve healing and health.

Electrolysis is the process of passing electric current through an electrolyte, thereby causing negative and positive ions to migrate to the positive and negative electrodes, respectively. Ions are created in at least two ways during the electrolytic reaction in water. Ions are formed as intermediaries as oxygen and hydrogen gases are formed from the water. Simultaneously, if proper metals are used for the anode and cathode, metal ions are released into the water as the anode and cathode degrade due to the ion exchange.

Several electrolytic devices are known in the art that increase the number of ions available in the water to draw out and bond with the undesirable metals and thereby remove them from the body. These device place an anode and a cathode in a bath of water and deliver current to the water, thereby creating ions. These prior art devices suffer several disadvantages, however, such as potential electrical shock hazard and severe overheating. Because the devices are powered by standard AC current during treatment, there is some risk that the patient would be shocked as a result of transient current spikes. The overheating is caused, in part, by high levels of salts or minerals in the water. These salts and minerals dissolve into their constituent ions, which increase the flow of current through the electrodes to an unsustainable level as the treatment proceeded. Elaborate fans and other moving parts have been devised to dissipate the heat.

Early devices had no control over the duration, polarity or intensity of the treatment, other than to pull the plug from the power supply. Thus, a treatment was limited in duration and control, and the devices burned out frequently. The current and voltage spikes common to commercial AC power supplies exacerbated the burn-out problem.

Therefore, it is an object of this invention to provide a device for increasing the number of ions available in a treatment to bond with undesirable chemicals and make them unavailable for reabsorption. It is also an object of this invention to provide a device for electrolytic hydrotherapy that reduces the potential electrical shock hazard. It is another object to provide a device that does not overheat under normal operation. It is a further object to provide a device that has control over the duration, polarity and intensity of the treatment.

SUMMARY OF THE INVENTION

The present invention is a device and method for increasing the number and type of ions in a hydrotherapy treatment to assist in removing unwanted chemicals from the body. A battery-powered array is submerged into a liquid foot bath to generate ions through electrolysis of the electrolyte. The array has at least two electrodes, one containing copper and/or zinc, the other steel. The device can be run in two polarity modes, thereby creating different types and quantities of ions and enabling the removal of different types of chemicals. The device uses a current and voltage regulator to deliver a regulated amount of current into the array regardless of the conductivity of the liquid, and electronic circuitry is used to control the duration, polarity and intensity of the treatment. Excessive heat is dissipated with a heat sink.

DETAILED DESCRIPTION OF THE INVENTION

Figure 1:
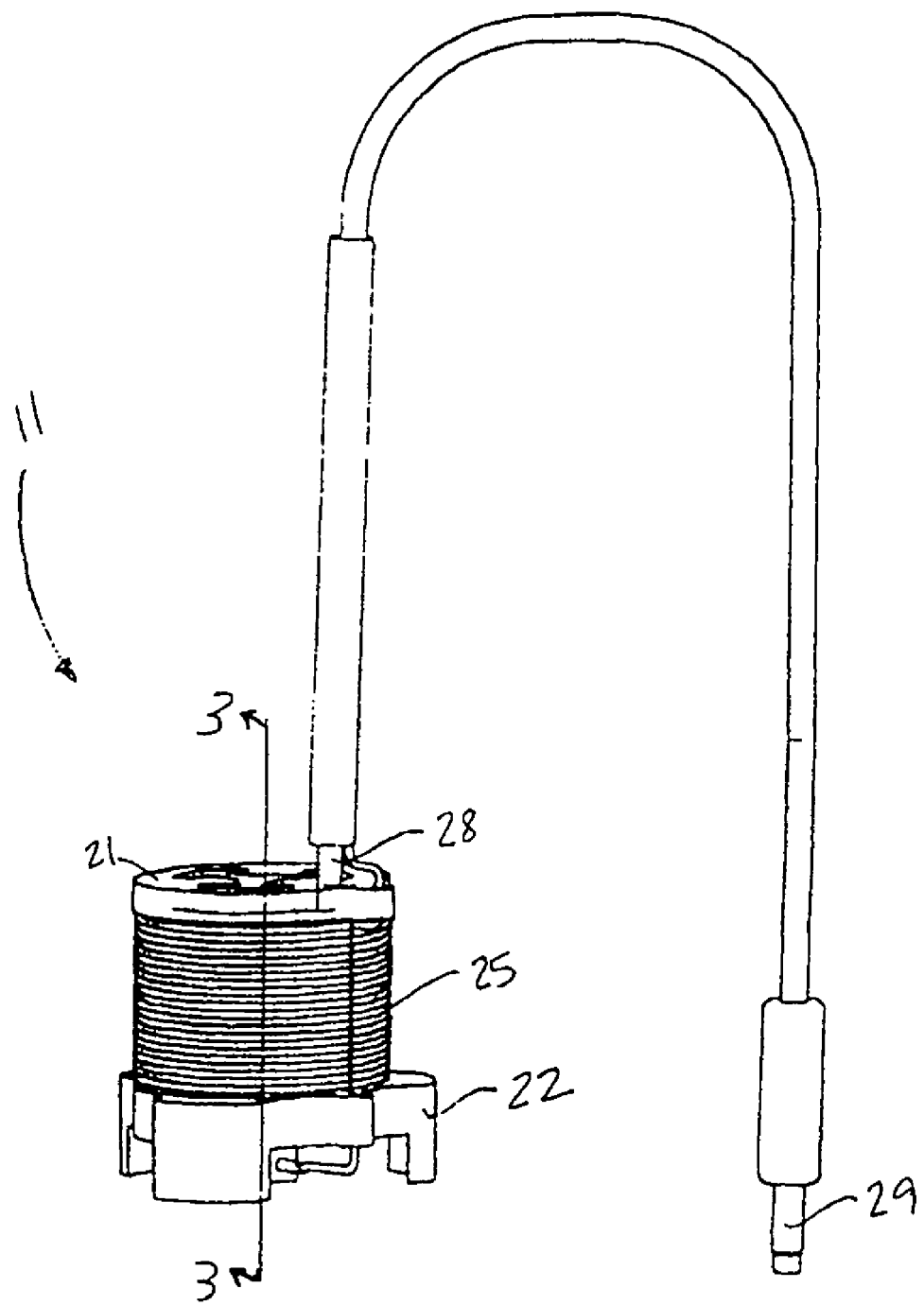
FIG. 1 is a perspective view of the array.
Figure 2:
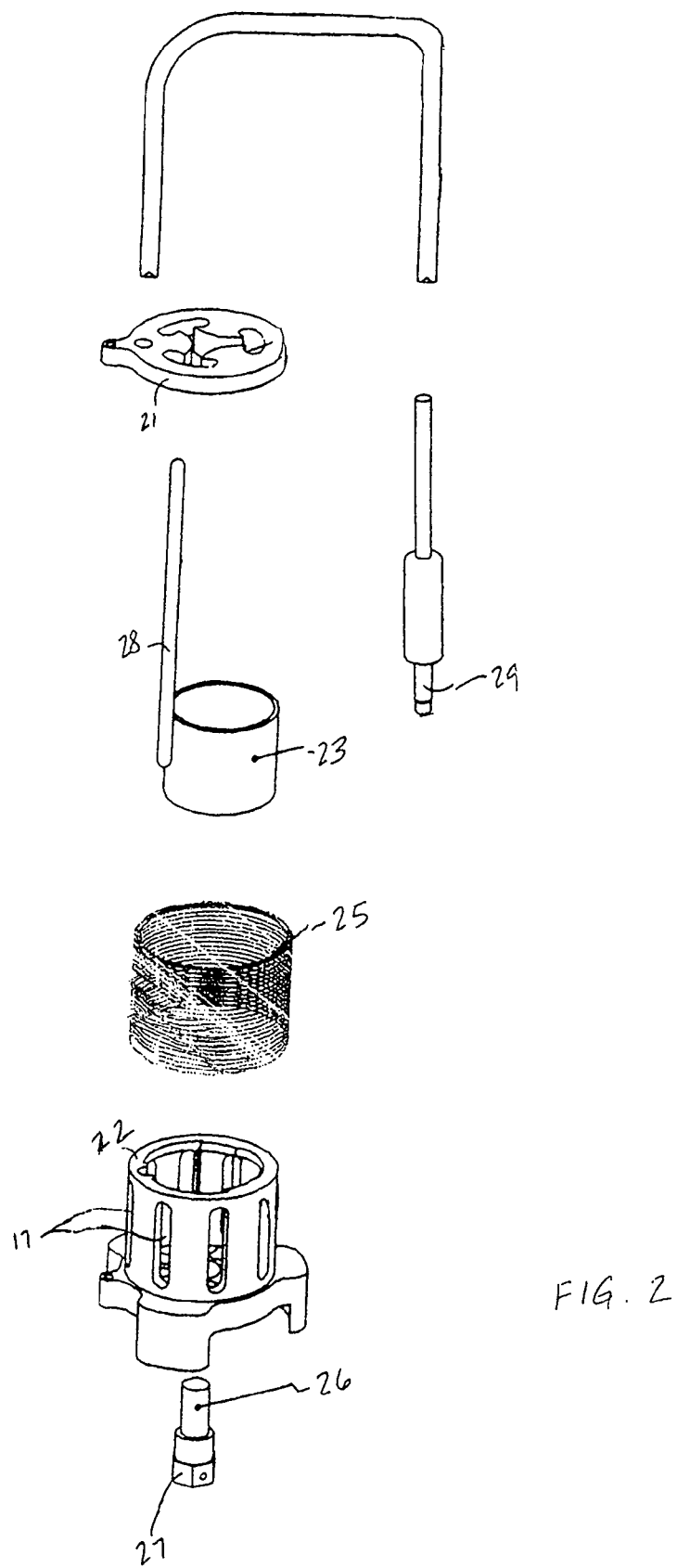
FIG. 2. is an exploded view of the array.

Referring to FIGS. 1-6, there is illustrated the preferred embodiment of the present invention, designated generally as 10, which is used to increase the number of ions available in a hydrotherapy treatment. FIG. 1 illustrates the array 11 used to electrolyze an electrolytic solution and thereby increase the number of ions in the solution. FIG. 2 illustrates the components of the array 11. A cap 21 and a base 22 form a housing to hold a first electrode 23 and a second electrode at a fixed distance from each other. The cap 21 and the base 22 have apertures in the array's top, bottom and sides through which the electrolytic solution can flow. Specifically, the solution should be able to freely flow between the first electrode and the second electrode, which is optimally achieved with side vents 17 on the base 22.

Figure 3:
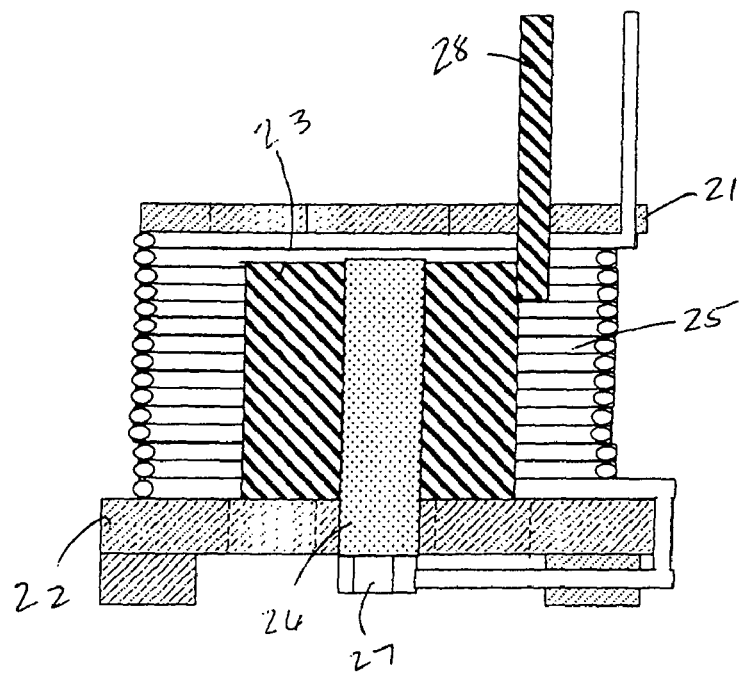
FIG. 3 is a cross-section of the array along line 3-3 of FIG. 1.

The first electrode 23 is connected to or integral with a rod 28, which is connected to a direct current source. The first electrode 23 is preferably tubular stainless steel, such as a stainless steel tube, a winding of stainless steel wire, or stack of stainless steel washers. The second electrode has two components, a tubular winding 25 and a post 26. The winding 25 has a first end and a second end. The first end of the winding 25 is connected to the post 26 with a fitting 27, and the second end is connected to a direct current source. The winding is preferably an actual winding of copper wire, but the tubular shape may also be achieved with a copper tube. Preferably the cap 21, the winding 25, the first electrode 23, and base 22 are substantially concentric around the post 26, as shown in FIG. 3.

Figure 4:
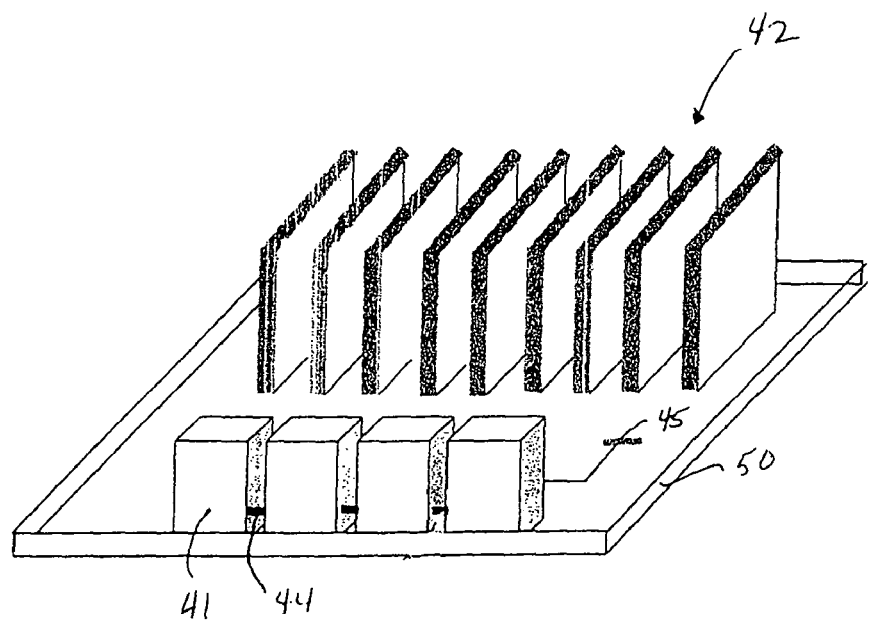
FIG. 4 illustrates the batteries and heat sink inside the bottom of the control box.
Figure 5:
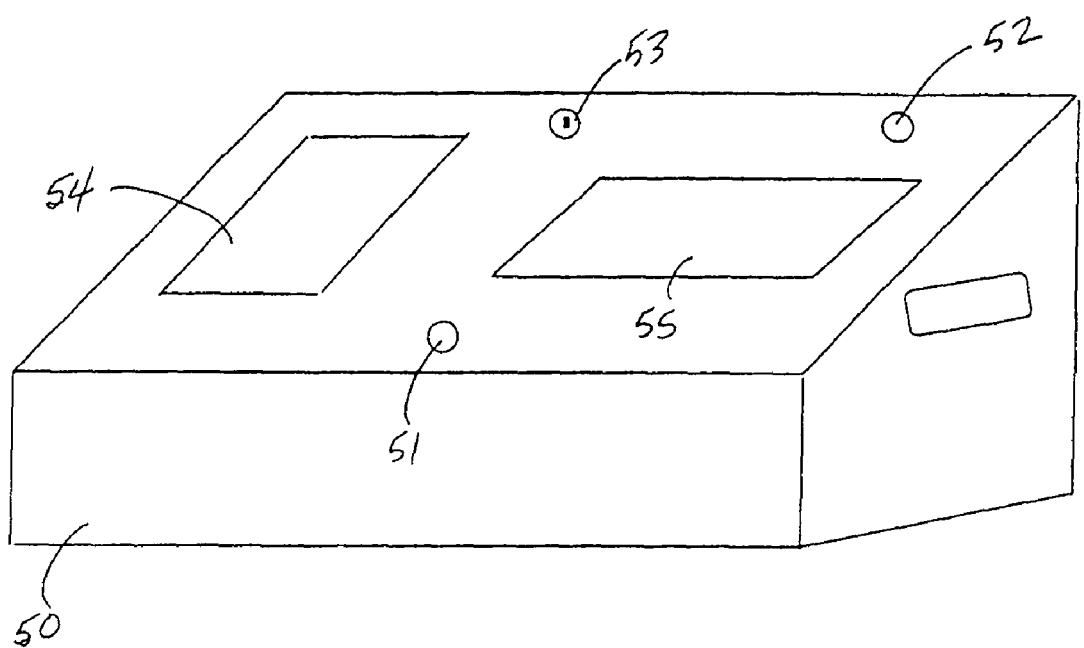
FIG. 5 is a front view of the control box.

The control box 50 houses the direct current source, a heat sink 42, circuitry for regulating current and voltage to the array 11, and circuitry for setting various parameters of the therapy. The direct current source may supply any size voltage, because circuitry in the control box 50 regulates the voltage to the desired level and outputs it to the array 11. Preferably, the direct current source is capable of supplying at least 24V DC, drawing less than 2 amps, which can be provided by battery or AC power supply converted to DC with the appropriate transformer. Preferably the direct current source is a set of four 6V rechargeable batteries, such as sealed lead acid batteries 41. FIG. 4 shows the batteries 41 seated in the bottom 40 of the control box 50, which are typically held in place with two large nylon or polypropylene battery holders (not shown). The batteries are connected in series with fuses 44 between adjacent cells, preferably 5 amp fuses. The fuses serve to prevent any inadvertent short-circuiting of the batter power source; a failure of the internal electronic circuitry or any internal wiring will blow a fuse, thereby preventing further power from being drawn from the batteries. Furthermore, any internal failure of the individual batteries themselves or failure of the insulating materials used within will also blow a fuse, thereby preventing any catastrophic damage to the device or the batteries themselves. The batteries can be recharged with standard AC current. Preferably, the control box 50 has a charge port 52 which is connected to AC current with an appropriate transformer or battery charger (not shown). The present device is not connected to AC power during use; instead, the device powered solely by direct current, preferably batteries.

A heat sink is housed in the control box 50 to dissipate any heat that may be generated. Preferably an aluminum heat sink 42 is used. The heat sink 42 comprises a series of aluminum plates, spaced apart to allow air flow between the plates.

The control box 50 also houses circuitry to regulate power to the array and control the treatment parameters of the device. Further, the circuitry provides the ability to store and recall several treatment protocols. Preferably the circuitry is digital, which is immune to drift or timing variations due to temperature changes and generates little heat. In the preferred embodiment, regulating circuitry regulates current and voltage to the array. This circuitry includes a current limiter 45 connected to the battery 41 which further serves to limit the maximum amount of current, regardless of the conductivity of the water.

The control box 50 also houses circuitry for controlling the parameters of the treatment, including the duration, mode and intensity. The parameter control circuitry includes an on/off switch that controls the delivery of power from the batteries 41 to the array 11; a timer for controlling the length of time the power is applied to the array; a switch for reversing which electrode the power is applied to; and a switch for varying the amount of power delivered to the array. The present device thereby allows an unlimited variation of positive and negative ion generation. The parameters are changed via a keypad 54 accessible from the front of the control box 50. Information is displayed on a display, preferably an liquid crystal display (LCD) 55, as is known the art. The device also includes a master on/off key switch 53. As with the current limiter, the timers and switches are electrical components known in the art, as individual components or in integrated circuits.

The quantity and type of ions determines the quantity and type of unwanted chemicals that can be drawn from the body. In the preferred embodiment, the first electrode is steel, a modified form of Fe, often containing many other constituent elements, as is known in the art. Preferably the first electrode 23 is stainless steel, being a low grade steel so as to erode, more slowly than ordinary steel, during operation of the device. The rod 28 is typically the same material as the first electrode, and preferably is low grade stainless steel. The winding 25, post 26 and fitting 27 may be made of the same material such as copper or zinc, however preferably the winding 25 is Cu and the post 26 is Zn. Preferably the fitting 27 that connects the winding and post together is brass, which is an alloy of mainly Cu and Zn.

Figure 6:
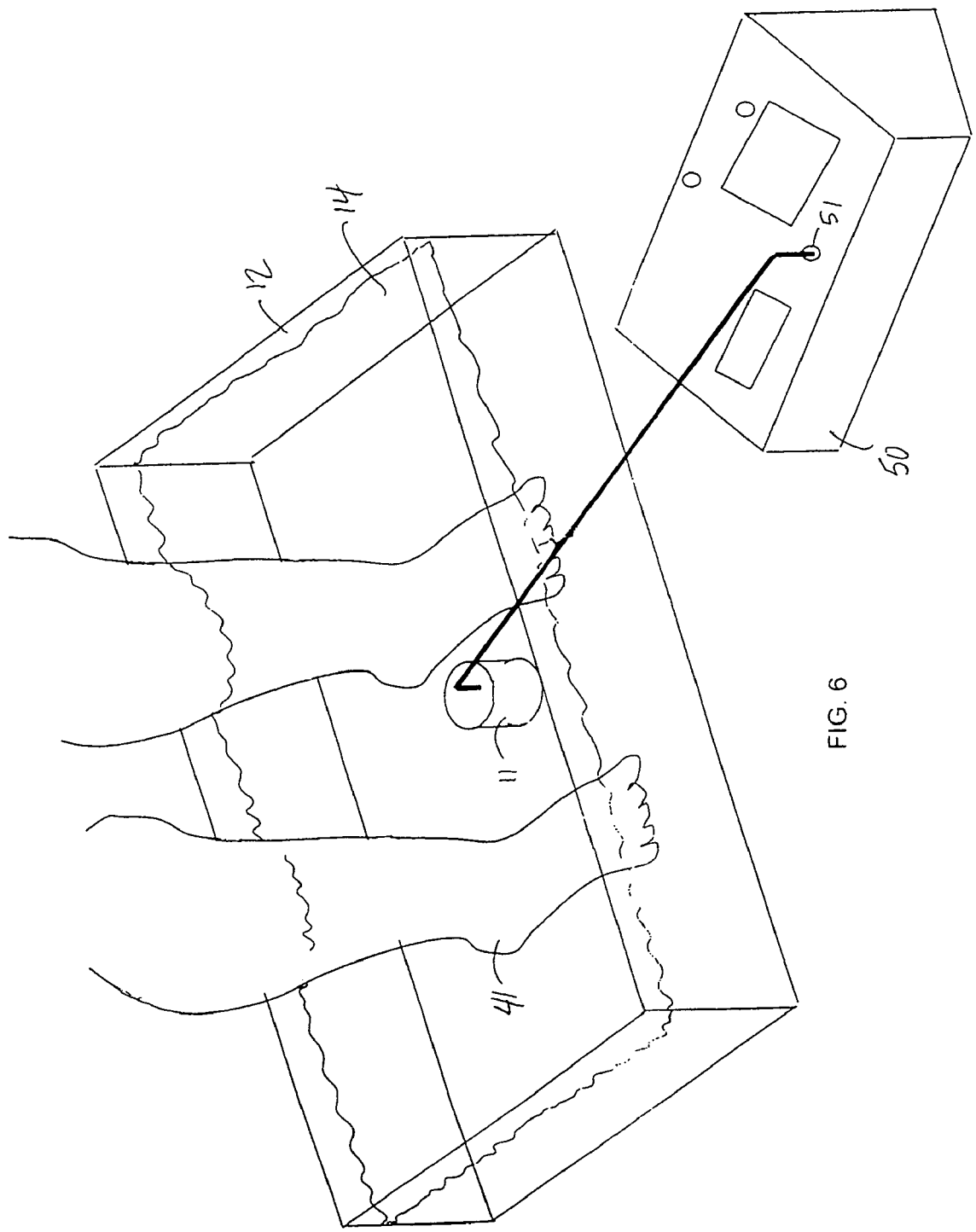
FIG. 6 illustrates a perspective view of the device in operation, with a patient's feet in a footbath straddling the array.

In use, the array 11 is submerged in an electrolytic solution contained in a vessel big enough to accommodate the desired part of a patient's body that is to be treated, or the entire body, if desired. FIG. 6 illustrates the preferred embodiment in which a patient's feet 41 are submerged in a foot bath 12 filled with water 14. The array 11 is attached to the control box 50 by inserting male plug 29 into a female port 51, thereby accessing the direct current source. Direct current is applied to the array 11 to electrolyze the water 14 which produces hydrogen gas bubbles at the positively charged electrode and oxygen gas bubbles at the negatively charged electrode. The polarity of treatment may be reversed, by switching the direct current source from one electrode to the other, thereby changing the polarity of the electrodes. Ions of at least Cu and Zn are formed in the water during the electrolysis as the electrodes degrade. The life of the electrodes will depend on many factors, including the duration and intensity of the treatments, the composition of the electrodes, and the composition of the electrolyte. For example, adding a catalyst or combination of catalysts, such as one or more salts, to the water may increase the number of ions in solution and decrease the life of the electrodes.

Various treatment protocols are employed, depending on the patient's needs. In Example 1, a patient's feet are submerged in a tap water bath along with the array. The system is programmed to apply 5 minutes of direct current at 1.5 amps to the first electrode (positive mode) and 5 minutes of current at 1.5 amps to the second electrode (negative mode). In Example 2, regular table salt, NaCl, is added to the electrolytic solution and a lower current is applied for a longer period of time than in Example 1. Examples 3-4 illustrate additional protocols.

EXAMPLE 1

| | |
|---|---|
| Electrolyte | tap water |
| Positive duration | 5 minutes at 1.5 amps |

-continued

| | |
|---|---|
| Negative duration | 5 minutes at 1.5 amps |

EXAMPLE 2

| | |
|---|---|
| Electrolyte | tap water with table salt added |
| Positive duration | 12 minutes at 0.75 amps |
| Negative duration | 12 minutes at 0.75 amps |

EXAMPLE 3

| | |
|---|---|
| Electrolyte | tap water |
| Positive duration | 15 minutes at 1.5 amps |
| Negative duration | 2 minutes at 1.5 amps |

EXAMPLE 4

| | |
|---|---|
| Electrolyte | tap water with sea salt added |
| Positive duration | 20 minutes at 1.5 amps |
| Negative duration | 0 minutes |

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

I claim:
1. A method of removing unwanted chemicals from a human body, the method comprising:
   a) submerging a part of the body in a vessel containing a liquid such that the unwanted chemicals are released from the body;
   b) submerging at least part of an array in the vessel, the array comprising:
      i. a first electrode comprising a steel tube;
      ii. a second electrode in electrolytic contact with the first electrode, the second electrode comprising:
         (1) a copper component disposed outside the steel tube;
         (2) a brass fitting connected to the copper component; and
         (3) a zinc component connected to the brass fitting and disposed inside the steel tube; and
      iii. a housing comprising a base and a cap connected to the base, the housing configured to hold the first electrode at a fixed distance from the second electrode;
   c) applying direct current of more than about 0.05 amps and less than about 2.0 amps to the array, the application of direct current causing metal ions which prevent reabsorption into the body of the unwanted chemicals to be released into the liquid; and
   d) removing the part of the body from the vessel after a predetermined period.

2. The method according to claim 1 wherein the direct current is applied to the first electrode.

3. The method according to claim 2 further comprising switching the direct current from the first electrode to the second electrode.

4. The method according to claim 1 wherein the direct current is supplied by one or more batteries.

5. The method according to claim 4 wherein the battery is a 6 volt battery.

6. The method according to claim 1 wherein the direct current is supplied by a plurality of batteries and the total voltage supplied by the batteries is at least 24 volts.

7. The method according to claim 1 wherein the liquid is water.

8. The method according to claim 1 wherein the predetermined period is 20 minutes or less.

9. The method according to claim 1 further comprising:
   a) stopping the direct current after a period of 20 minutes or less; and
   b) repeating the steps of the method after more than 24 hours have elapsed from removing the part of the body from the vessel.

* * * * *